United States Patent [19]

Latif et al.

[11] Patent Number: 4,889,708

[45] Date of Patent: Dec. 26, 1989

[54] FUMIGANT SYSTEM

[75] Inventors: Sherif Latif, Ashfield; Robert F. Ryan, Sans Souci, both of Australia

[73] Assignee: The BOC Group, Inc., Murray Hill, N.J.

[21] Appl. No.: 314,311

[22] Filed: Feb. 22, 1989

Related U.S. Application Data

[60] Continuation of Ser. No. 245,876, Sep. 16, 1988, abandoned, which is a division of Ser. No. 877,824, Jun. 24, 1986.

[30] Foreign Application Priority Data

Jun. 27, 1985 [AU] Australia .............................. PH1239

[51] Int. Cl.$^4$ ........................................... H01N 25/02
[52] U.S. Cl. ....................................... 424/43; 422/28; 424/40; 424/601; 43/125; 43/132.1
[58] Field of Search .................... 424/43, 128, 40; 422/28; 43/132.1, 125, 129, 900

[56] References Cited

U.S. PATENT DOCUMENTS

| | | | |
|---|---|---|---|
| 2,007,738 | 7/1935 | Baer | 99/9 |
| 2,826,527 | 3/1958 | Huter | 167/14 |
| 3,406,082 | 10/1968 | Plant | 99/225 |
| 3,767,362 | 10/1973 | Griffin et al. | 21/58 |
| 4,059,048 | 11/1977 | Dickson | 99/482 |
| 4,069,308 | 1/1978 | Tanaka | 424/43 |
| 4,200,656 | 8/1980 | Ghen et al. | 426/331 |
| 4,200,657 | 4/1980 | Cook | 426/419 |
| 4,215,508 | 8/1980 | Allen et al. | 43/131 |
| 4,325,296 | 4/1982 | Ukai et al. | 99/468 |
| 4,421,742 | 12/1983 | Friemel et al. | 424/128 |
| 4,579,714 | 4/1986 | Gunn | 426/335 |
| 4,597,218 | 7/1986 | Friemel et al. | 43/131 |

FOREIGN PATENT DOCUMENTS

| 494198 | 12/1977 | Australia .............................. 87/18 |
|---|---|---|
| 1726583 | 5/1981 | Australia . |
| 1554774 | 6/1976 | United Kingdom . |

OTHER PUBLICATIONS

Airco Special Gases and Equipment Catalog, Copyright 1982, Cover, pp. 39, 86, 87.

K. H. Buchel, "Chemistry of Pesticides", Wiley-Interscience, pp. 160–161.

*Primary Examiner*—Thurman K. Page
*Assistant Examiner*—P. Prater
*Attorney, Agent, or Firm*—David A. Draegert; Larry R. Cassett

[57] ABSTRACT

A fumigant composition comprising a pressurized mixture of a diluent gas and phosphine in predetermined proportions within a container adapted for release of gaseous fumigant. A method of preparing the composition comprises the steps of pumping a predetermined quantity of phosphine under pressure into the container and filling the container with a liquified diluent gas. A method of fumigating a substantially closed space by liberating the composition is also disclosed.

6 Claims, No Drawings

FUMIGANT SYSTEM

This is a continuation of application Ser. No. 245,876, filed Sept. 16, 1988, now abandoned, which is a division of application Ser. No. 877,824 filed June 24, 1986.

This invention relates to the fumigation of stored produce, such as grains and other commodities which are likely to be stored in bulk for long periods, to protect it from damaging infestation by insect or other living pests.

More particularly the invention relates to fumigation when the toxic agent used is the gas phosphine ($PH_3$).

The currently used method of fumigating with $PH_3$ in silos and similar bulk storage structures has been to generate $PH_3$ within the structure by the hydrolysis of phosphides, such as those of calcium, magnesium, aluminium, zinc and tin, by exposing the phosphides in the structure for reaction with naturally occurring atmospheric moisture.

The phosphides are commercially available in admixture with other chemicals in the form of beads, tablets or sachets, all of which are embraced by the term pellets as used herein. In use the pellets are distributed within the storage structure and simply left to decompose and gradually release the $PH_3$. Although this method of fumigating has been widely used for quite a considerable time it has several severe disadvantages.

For example, both the pellets and the $PH_3$ they tend spontaneously to generate are highly toxic to mammals. $PH_3$ is flammable and the reaction of the phosphides in the pellets with moisture is exo-thermic to the extent that the pellets constitute a fire and explosion hazard ii contacted by free water. These factors create difficulties in the storage of the pellets prior to use. Those difficulties are enhanced by the need to keep the pellets sealed from the atmosphere to prevent them losing their efficacy.

Furthermore, in use it is necessary for the pellets to be spaced apart to prevent excessive localised heat generation which may start a fire and for the pellets to include further chemicals which react to generate diluent non-flammable gases intended to mix with the $PH_3$ to produce a less flammable mixture. However neither safeguard may be effective in the presence of excessive moisture, especially if, as sometimes occurs, spontaneously flammable di- or higher phosphines are generated in any substantial quantity.

A commonly used chemical for the production of the diluent gas is ammonium carbamate which decomposes to produce ammonia and carbon dioxide. The latter is harmless but the former reacts with copper and copper alloys to an extent requiring protective measures to be taken to prevent corrosion damage to electrical wiring, switches, meters, alarm systems and electronic monitoring apparatus required in major silos holding large quantities of valuable produce.

The pellets are usually formulated so that the proportion of $PH_3$ in the normally produced gas mixture is below the accepted Lower Explosive Limit, which hitherto has been taken as about 1.79% to 1.8% $PH_3$ by volume in air. This is claimed to overcomes the flammability hazard, but, on the other hand, in the dry atmospheres sometimes encountered in inland Australia the release rate of phosphine may be depressed by that safeguard to a level at which the time taken for the phosphine concentration in the silo to reach a sufficiently toxic level is unduly long. Indeed it sometimes happens that the Produce has to be shipped from storage before the reaction is complete so that residual quantities of toxic pellets have to be collected and removed before shipment of the produce, which is frequently a foodstuff intended for human consumption, can safely proceed.

An object of the present invention is to lessen the uncertainties inherent in the on site activities connected with fumigating with pellets of $PH_3$ as indicated above.

The invention achieves that objective by providing a factory prepared fumigant composition containing $PH_3$ which may be released directly as a gas into the space to be fumigated thereby avoiding any time delay in its taking effect and eliminating the possibility of there being any solid toxic residues.

In one aspect the invention consists in a fumigant composition comprising a pressurized mixture of a diluent gas and phosphine in predetermined proportions within a container adapted for release of gaseous fumigant.

In another aspect the invention consists of a method of producing a pressurized fumigant composition within a container adapted for release of gaseous fumigant comprising the steps of pumping a predetermined quantity of phosphine under pressure into the container and filling the container with a liquified diluent gas.

In a further aspect the invention consists in a method of fumigating a substantially closed space comprising the steps of filling a container adapted for release of gaseous fumigant with a pressurized mixture of a diluent gas and phosphine in predetermined proportions; and liberating the mixture into said space.

The diluent gas is preferably carbon dioxide ($CO_2$), but may be another inert gas, such as nitrogen or argon, or a mixture thereof. As used herein an inert gas means a non-flammable gas that does not react with phosphine.

In extensive experiments leading to the present invention it was found, at least when the diluent gas is $CO_2$, that higher concentrations of $PH_3$ than was previously thought possible may be tolerated without the liberated gas mixture being an explosive hazard. Thus in accordance with the invention the mixture may contain up to 3% by volume of $PH_3$.

Where the diluent gas is carbon dioxide the pressure of the gas mixture within the container may be up to 6 MPa.

Where the diluent gas is nitrogen or argon the pressure of the gas mixture within the container may be up to 16 MPa.

Thus the invention provides a standardized composition having a precise and known concentration of $PH_3$. Therefore, an operator may readily calculate the minimum quantity Of fumigant that has to be released into any particular closed space to achieve the required concentration therein suited to the nature of the produce, the amount thereof and the pest to be destroyed. There is no need to make allowance for produce temperature and moisture content as must be done when using pellets, and as the fumigant composition is dry it may be used with powdered produce, such as milled grain for example.

During manufacture of the fumigant $PH_3$ as a gas may be pumped under pressure into a container in the form of an empty cylinder equipped with an educator tube and prepurged with $CO_2$. A normal $CO_2$ cylinder commonly known as a G size cylinder customarily holds 31 kg of liquid $CO_2$ with a gaseous head space to allow for pressure increase up to 6 MPa within the cylinder in the event of temperature rise. This corresponds to approximately 16.5 m³ of CO₂ gas at atmospheric temperature and pressure. Thus, if, say, 2% PH₃ by weight (2.6% by volume) is required in the fumigant gas some 440 liters of PH₃ at atmospheric temperature and pressure has to be pumped into the cylinder. That is about 620 g of PH₃.

The PH₃ charged cylinder may then be filled with 30.4 kg of liquid CO₂.

Using conventional proprietary gas purification techniques, impurities are preferably removed from the PH₃ before it is pumped into the cylinder.

The fumigant gas may be conducted from the cylinder by pipe for direct injection into the mass of the produce which is known as a "one shot" technique or may be applied using a "flow through" technique in which the mixture is diluted to as low as 10 parts per million (ppm) phosphine. The flow through technique has particular application where a high level of gas tightness of the produce storage vessel cannot be achieved. Similar results are achieved using both the one shot and flow through techniques notwithstanding that the latter uses a lower phosphine concentration. This is because a constant lower concentration is applied for a sufficient time for the generally more tolerant egg or pupal stages of the pests to develop to the generally less tolerant larval and adult stages.

In accordance with the flow through technique the fumigant gas mixture from a high pressure cylinder is introduced at a calculated rate, using a conventional needle valve and flow meter arrangement, into a stream of air supplied by a portable air blower. The stream of air comprising a diluted mixture of fumigant is conducted by pipe for injection in the produce by outlet nozzles extending into the vessel containing the produce or can be directed into aeration manifolds or the like frequently found in grain silos, storage bins and the like.

The supply of the fumigant may be manually controlled or may be operated by a timer device for the automatic release of fumigant at selected intervals for desired periods.

The following examples illustrate how the amount of fumigant required for the two described techniques of application is calculated.

EXAMPLE 1

"One Shot" technique

Silo Volume: 50 m³
Silo Capacity: 56 tonnes of wheat
Using the recommended dosage of 100 g.hr/m³ PH₃ which is equivalent to concentration × time (ct) product of 5000 g.hr/m³ of the 2% by weight pH₃ mixture and an exposure time of 7 days (170 hours) the mixture dose is calculated as follows:

$$\text{Concentration} \times \text{time (ct) product} = 5000 \text{ g} \cdot \text{hr/m}^3$$

$$\frac{\text{The mixture (g)} \times 170 \text{ (hrs)}}{50 \text{ (m}^3\text{)}} = 5000 \text{ g} \cdot \text{hr/m}^3$$

i.e. dose of the mixture required $= \frac{5000 \times 50}{170} = 1470$ gms (app. 1.5 kg)

EXAMPLE 2

"Flow-Through" Technique

Silo Volume: 50 m³
Silo Capacity: 56 tonnes of wheat
Using a flow-through dose of 0.5 g/m³ of the 2% by weight pH₃ mixture, with an exposure time to 30 days and flow of one volume change/day gives a mixture dose of:

$$= 50 \text{ (m}^3\text{, volume)} \times 1 \text{ (volume change/day)} \times$$
$$30 \text{ days)} \times 0.5 \text{ g/m}^3$$
$$= 1500 \text{ m}^3 \times 0.5 \text{ g/m}^3 = 750\text{g}$$

EXAMPLE 3

Technique for horizontal (fabric covered) grain storage

Silo Volume: 48,000 m³
Silo Capacity: 21,800 tonnes of wheat (28,300 m³/59% of volume)
Storage factor: 0.77 tonne/m³
"Air" Volume:

| | |
|---|---|
| Volume above grain (41% of total volume) = | 19,700 m³ |
| + Intergranular volume (59% × 0.38) = | 10,800 m³ |
| | 30,500 m³ |

Assume the above storage is treated with six (6) 'G' size high pressure cylinders (31 kg. nett. wt) of 2% by weight pH₃ mixture. The concentration profile will vary from an initial high of 134 ppm phosphine to a final value which will be mainly influenced by penetration of enclosing fabric (leaks) and absorption by the grain (not significant) namely:

(i) Within 30 minutes (time to discharge six cylinders) the concentration in volume above grain (19,700 m³) may be calculated:

$$\frac{6 \text{ (cylinders)} \times 620 \text{ g (grams of PH}_3\text{/cylinder)}}{19,700 \text{ m}^3 \text{ (Volume above grain)}} =$$

$$0.189 \text{ g/m}^3 \text{ or } 134 \text{ ppm}$$

(ii) When gas has diffused into the intergranular volume the concentration in the total "Air" volume (30,500 m³) may be calculated:

$$\frac{6 \text{ (cylinders)} \times 620 \text{ g (grams of PH}_3\text{/cylinder)}}{30,500 \text{ m}^3 \text{ (Total "air" Volume)}} =$$

$$0.122 \text{ g/m}^3 \text{ or } 87 \text{ ppm}$$

What is claimed is:

1. A nonflammable fumigant system, which comprises:
   a liquified gas contains adapted for release of a gaseous fumigant; and
   a pressurized gaseous fumigant mixture of a liquified inert gas and phosphine charged into said liquified gas container, said phosphine being present in an amount to provide up to about 3% by volume phosphine in released gaseous fumigant.

2. The nonflammable fumigant system as claimed in claim 1 wherein said phosphine is present in an amount of from 1.8% to 3% by volume.

3. The nonflammable fumigant system as claimed in claim 2 wherein said liquified inert gas is carbon dioxide.

4. The nonflammable fumigant system as claimed in claim 2 wherein said liquified inert gas is nitrogen or argon.

5. The nonflammable fumigant system as claimed in claim 3 wherein pressure of said gaseous fumigant mixture is up to 6 MPa.

6. The nonflammable fumigant system as claimed in claim 4 wherein pressure of said pressurized gaseous mixture is up to 16 MPa.

* * * * *

UNITED STATES PATENT AND TRADEMARK OFFICE
CERTIFICATE OF CORRECTION

PATENT NO. : 4,889,708
DATED : December 26, 1989
INVENTOR(S) : Latif et al.

It is certified that error appears in the above-identified patent and that said Letters Patent is hereby corrected as shown below:

Column 1, line 23: "arc" should read --are--

Column 1, line 33: "ii" should read --if--

Column 2, line 53: "Of" should read --of--

Column 2, line 64: "educator" should read --eductor--

Column 3, line 65: "requived" should read --required--

Column 4, line 60: "contains" should read --container--

Signed and Sealed this

Ninth Day of July, 1991

Attest:

HARRY F. MANBECK, JR.

Attesting Officer

Commissioner of Patents and Trademarks